(12) United States Patent
Chervitz et al.

(10) Patent No.: US 6,499,486 B1
(45) Date of Patent: Dec. 31, 2002

(54) METHOD FOR RECONSTRUCTING A LIGAMENT

(75) Inventors: Alan Chervitz, Palm Harbor, FL (US); T. Wade Fallin, Hyde Park, UT (US); Daniel F. Justin, Logan, UT (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/626,506

(22) Filed: Jul. 27, 2000

Related U.S. Application Data

(60) Provisional application No. 60/146,253, filed on Jul. 29, 1999.

(51) Int. Cl.$^7$ ................................................ A61B 19/00
(52) U.S. Cl. ..................................... 128/898; 623/13.11
(58) Field of Search ........................... 128/898; 600/36; 623/13.11–13.2

(56) References Cited

U.S. PATENT DOCUMENTS

| 5,139,520 A | 8/1992 | Rosenburg |
| 5,393,302 A | 2/1995 | Clark et al. |
| 5,601,562 A | 2/1997 | Wolf et al. |
| 5,918,604 A | 7/1999 | Whelan |

FOREIGN PATENT DOCUMENTS

| WO | WO 99/15095 | * 4/1999 | ........... A61B/17/76 |

* cited by examiner

Primary Examiner—Corrine McDermott
Assistant Examiner—Thomas Barrett
(74) Attorney, Agent, or Firm—Pandiscio & Pandiscio, P.C.

(57) ABSTRACT

A method for reconstructing a ligament. In one form of the invention, there is disclosed a method for securing a graft ligament in a bone tunnel, the method comprising the steps of: (1) forming a first bone tunnel in a bone, and forming a second bone tunnel in the same bone, the second bone tunnel being transverse to, and intersecting, the first bone tunnel; (2) positioning a flexible member in the second transverse bone tunnel so that the flexible member extends across the first bone tunnel, and positioning the graft ligament in the first bone tunnel, independently of the flexible member, so that the graft ligament is looped over the flexible member; and (3) positioning a crosspin over the flexible member and in the second transverse bone tunnel so that the graft ligament is looped over, and may be supported by, the crosspin.

6 Claims, 14 Drawing Sheets

METHOD FOR RECONSTRUCTING A LIGAMENT

REFERENCE TO PENDING PRIOR PATENT APPLICATION

This patent application claims benefit of pending prior U.S. Provisional Patent Application Serial No. 60/146,253, filed 07/29/99 by Alan Chervitz et al. for METHOD TO DELIVERING AN ACL GRAFT IN THE KNEE, which patent application is hereby incorporated herein by reference.

FIELD OF THE INVENTION

This invention relates to medical devices and procedures in general, and more particularly to medical devices and procedures for reconstructing a ligament.

BACKGROUND OF THE INVENTION

A ligament is a piece of fibrous tissue which connects one bone to another.

Ligaments are frequently damaged (e.g., detached or torn or ruptured, etc.) as the result of injury and/or accident. A damaged ligament can impede proper motion of a joint and cause significant pain.

Various procedures have been developed to repair or replace a damaged ligament. The specific procedures used depend on the particular ligament which is to be restored and on the extent of the damage.

One ligament which is frequently damaged as the result of injury and/or accident is the anterior cruciate ligament (ACL). Looking now at FIG. 1, the ACL 5 extends between the top of the tibia 10 and the bottom of the femur 15. A damaged ACL can cause instability of the knee joint and cause substantial pain and arthritis.

Numerous procedures have been developed to restore the ACL through a graft ligament replacement. In general, and looking now at FIG. 2, these ACL replacement procedures involve drilling a bone tunnel 20 through tibia 10 and up into femur 15. Then a graft ligament 25, consisting of a harvested or artificial ligament or tendon(s), is passed through the tibial portion 30 of tunnel 20 (sometimes referred to as "the tibial tunnel"), across the interior of the joint, and up into the femoral portion 35 of tunnel 20 (sometimes referred to as "the femoral tunnel"). Then a distal portion of graft ligament 25 is secured in femoral tunnel 35, and a proximal portion of graft ligament 25 is secured in tibial tunnel 30.

There are numerous ways in which graft ligament 25 may be positioned in tunnel 20 and secured in position.

One such way is disclosed in U.S. Pat. No. 5,918,604, issued 07/06/99 to Whelan for METHOD OF LOADING TENDONS INTO THE KNEE. According to this patent, the ligament may be towed up tibial tunnel 30 and femoral tunnel 35 and then secured in femoral tunnel 35 with a crosspin.

More particularly, and looking now at FIG. 3, the bone tunnel 20 is formed by drilling through tibia 10 and up into femur 15, whereby to form tibial tunnel 30 and femoral tunnel 35. Then a transverse bone tunnel 40 is formed in femur 15 so that transverse bone tunnel 40 intersects femoral tunnel 35. Bone tunnel 20 bifurcates transverse bone tunnel 40 into two tunnel portions, a first transverse bone tunnel portion 45 and a second transverse bone tunnel portion 50.

After transverse bone tunnel 40 has been formed, a flexible member 55 is used to draw graft ligament 25 up into place.

More particularly, according to the aforementioned U.S. Pat. No. 5,918,604, this is done by threading flexible member 55 through transverse bone tunnel 40. Then a crochet-hook device (not shown in FIG. 3) is passed up tibial tunnel 30, across the interior of the knee joint, and up femoral tunnel 35. The crochet-hook device is used to hook flexible member 55 at the intersection of bone tunnel 20 and transverse bone tunnel 40. Then the crochet-hook device is used to pull flexible member 55 down femoral tunnel 35, across the interior of the knee joint, down tibial tunnel 30, and out the front side of tibia 10. Next, graft ligament 25 is looped over flexible member 55 (FIG. 3). One or both free ends of flexible member 55 is/are then pulled away from femur 15, whereby to pull flexible member 55, and hence the looped graft ligament 25, up tibial tunnel 30, across the interior of the knee joint, and then up into femoral tunnel 35 (FIG. 4).

Once flexible member 55 and graft ligament 25 have assumed the position shown in FIG. 4, the graft ligament may be retained in that position by passing a cannulated crosspin 60 over flexible member 55 into transverse bone tunnel 40 so that the crosspin extends under graft ligament 25 and supports the looped graft ligament within femoral tunnel 35. Then flexible member 55 is withdrawn from the surgical site.

Unfortunately, the method taught in U.S. Pat. No. 5,918,604 suffers from a number of drawbacks.

For one thing, use of this method can result in erosion of the patient's bone. More particularly, and looking now at FIG. 5, flexible member 55 must first be drawn down femoral tunnel 35, across the interior of the knee joint, and then down tibial tunnel 30 in order to pick up graft ligament 25; and then later, flexible member 55 must be drawn back up tibial tunnel 30, across the interior of the knee joint, and then back up femoral tunnel 35 in order to carry graft ligament 25 into position. These actions cause flexible member 55 to engage the bone which is located at the intersection of femoral tunnel 35 and transverse bone tunnel 40, i.e., to engage the bone edges 65 (FIG. 5). This engagement between flexible member 55 and bone edges 65 can cause bone edges 65 to be eroded. This erosion can be particularly significant where substantial forces are required to draw flexible member 55 out of bone tunnel 20 (e.g., where a metallic flexible member 55 is used); or when substantial forces are required to draw flexible member 55 and graft ligament 25 up bone tunnel 25 (e.g., where graft ligament 25 makes a tight engagement with the walls of bone tunnel 20).

For another thing, the method taught in U.S. Pat. No. 5,918,604 can be tedious to practice. More particularly, when flexible member 55 and ligament graft 25 are in the position shown in FIG. 5, flexible member 55 will form the angle θ; however, when flexible member 55 and ligament graft 25 are in the position shown in FIG. 6, flexible member 55 will form a different angle θ. In this respect it will be appreciated that it will be considerably more difficult to pull graft ligament 25 upwards as the angle θ increases from the position shown in FIG. 5 to the position shown in FIG. 6.

OBJECTS OF THE INVENTION

As a result, an object of the present invention is to provide an improved method for reconstructing a ligament.

And another object of the present invention is to provide an improved method for reconstructing a ligament which substantially avoids the problems associated with the prior art.

SUMMARY OF THE INVENTION

These and other objects of the present invention are addressed by a novel method for reconstructing a ligament.

In one preferred form of the invention, the invention comprises a method for securing a graft ligament in a bone tunnel, the method comprising the steps of: (1) forming a first bone tunnel in a bone, and forming a second bone tunnel in the same bone, the second bone tunnel being transverse to, and intersecting, the first bone tunnel; (2) positioning a flexible member in the second transverse bone tunnel so that the flexible member extends across the first bone tunnel, and positioning the graft ligament in the first bone tunnel, independently of the flexible member, so that the graft ligament is looped over the flexible member; and (3) positioning a crosspin over the flexible member and in the second transverse bone tunnel so that the graft ligament is looped over, and may be supported by, the crosspin.

BRIEF DESCRIPTION OF THE DRAWINGS

The above and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE INVENTION

The present invention comprises a novel method for reconstructing a ligament.

Figure 1:
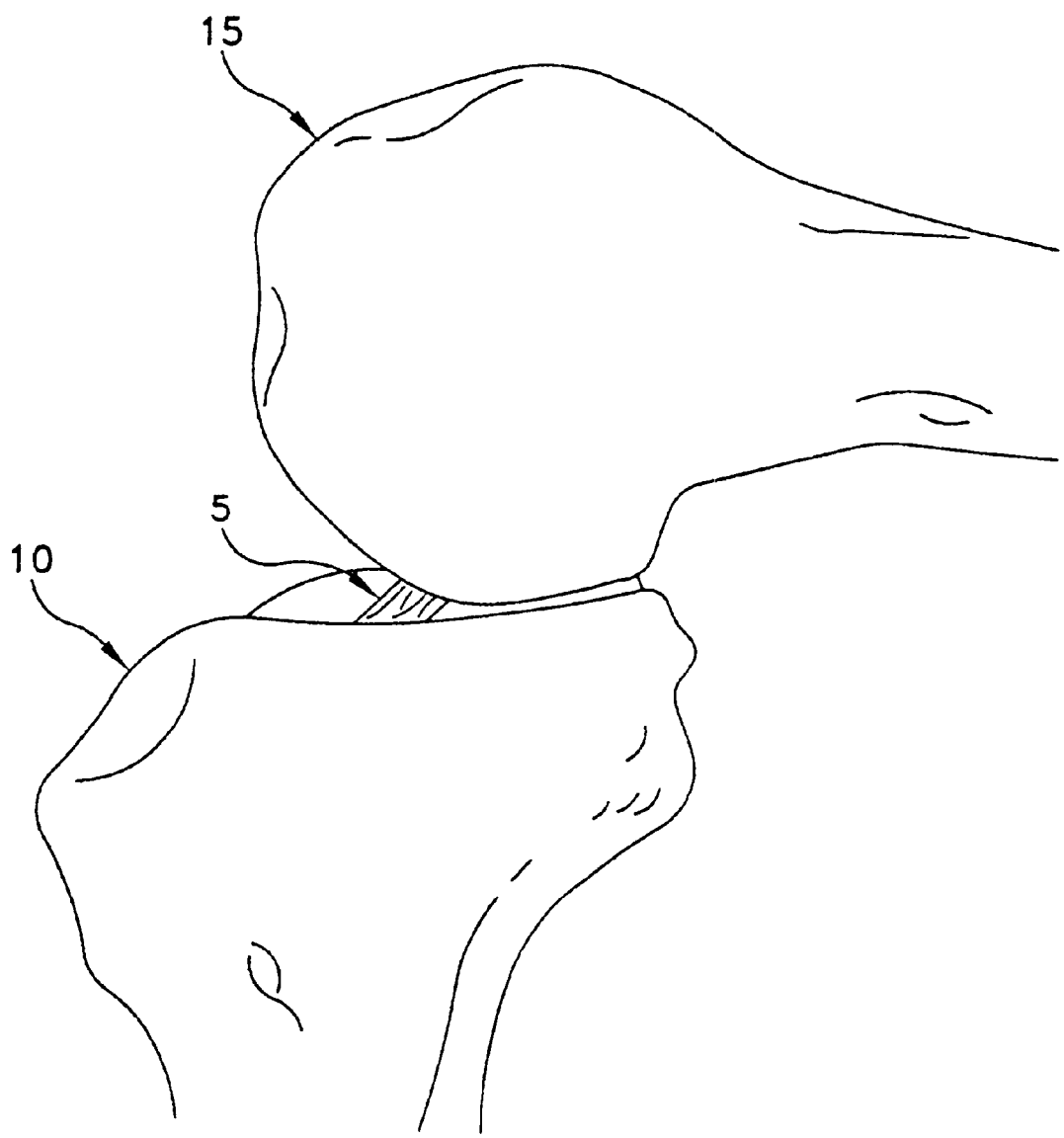
FIG. 1 is a schematic side view of a knee joint, showing an ACL extending between the top of the tibia and the bottom of the femur.
Figure 2:
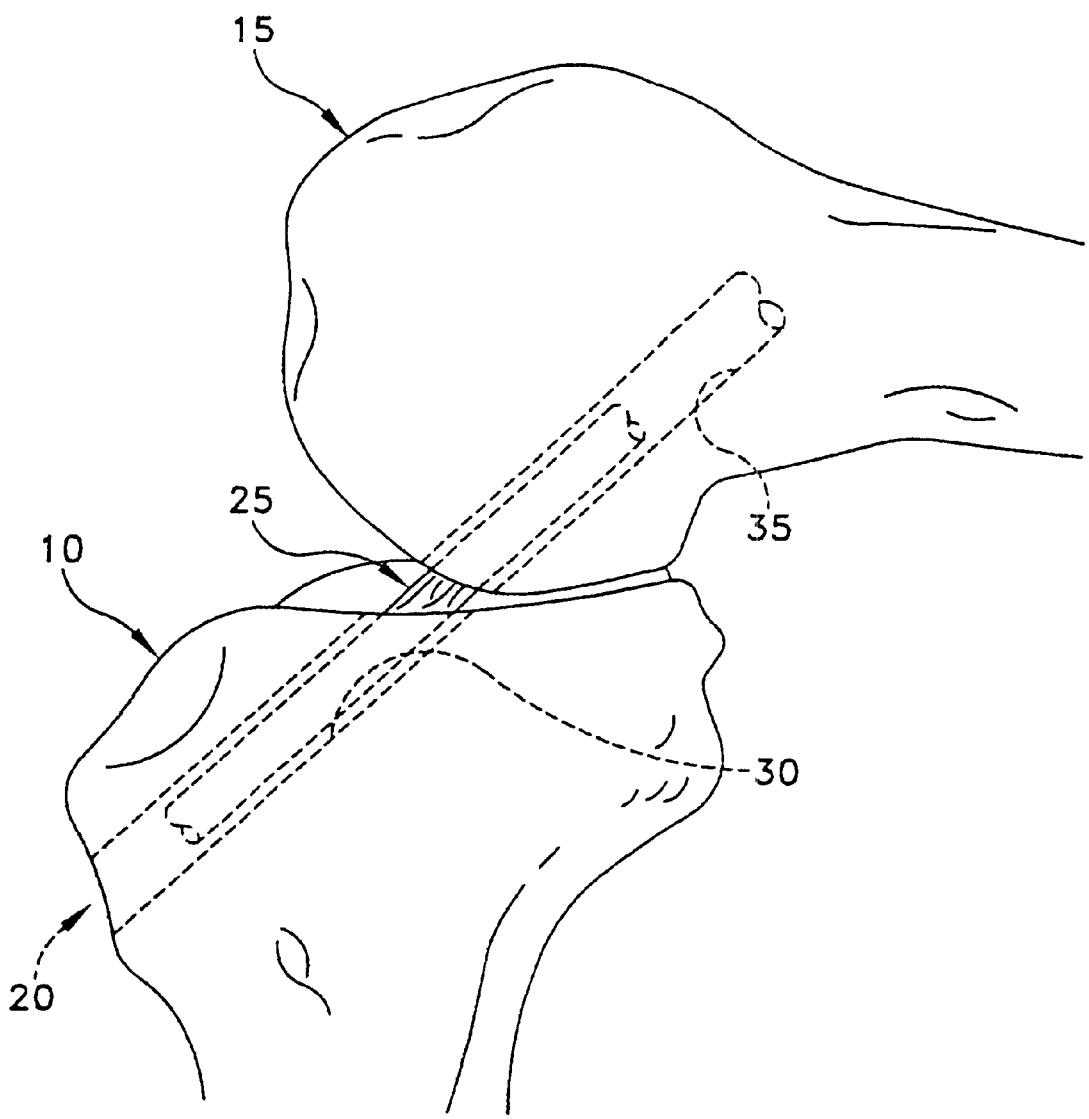
FIG. 2 is a schematic side view of the same knee joint, except showing portions of an ACL reconstruction.
Figure 3:
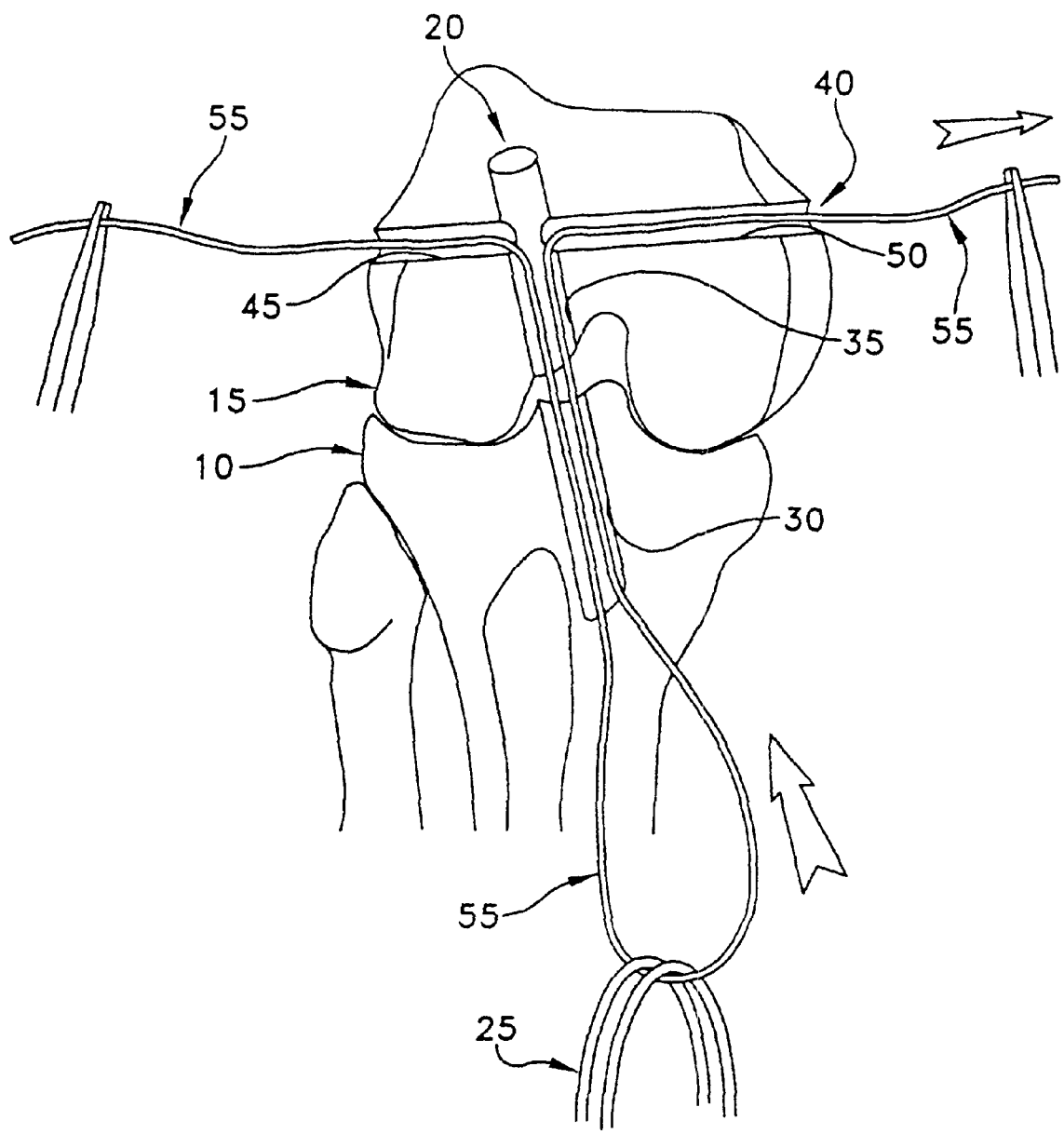
FIGS. 3–6 are schematic front views of a knee joint, illustrating various aspects of a prior art procedure for positioning a graft ligament in a bone tunnel and securing it in position.
Figure 4:
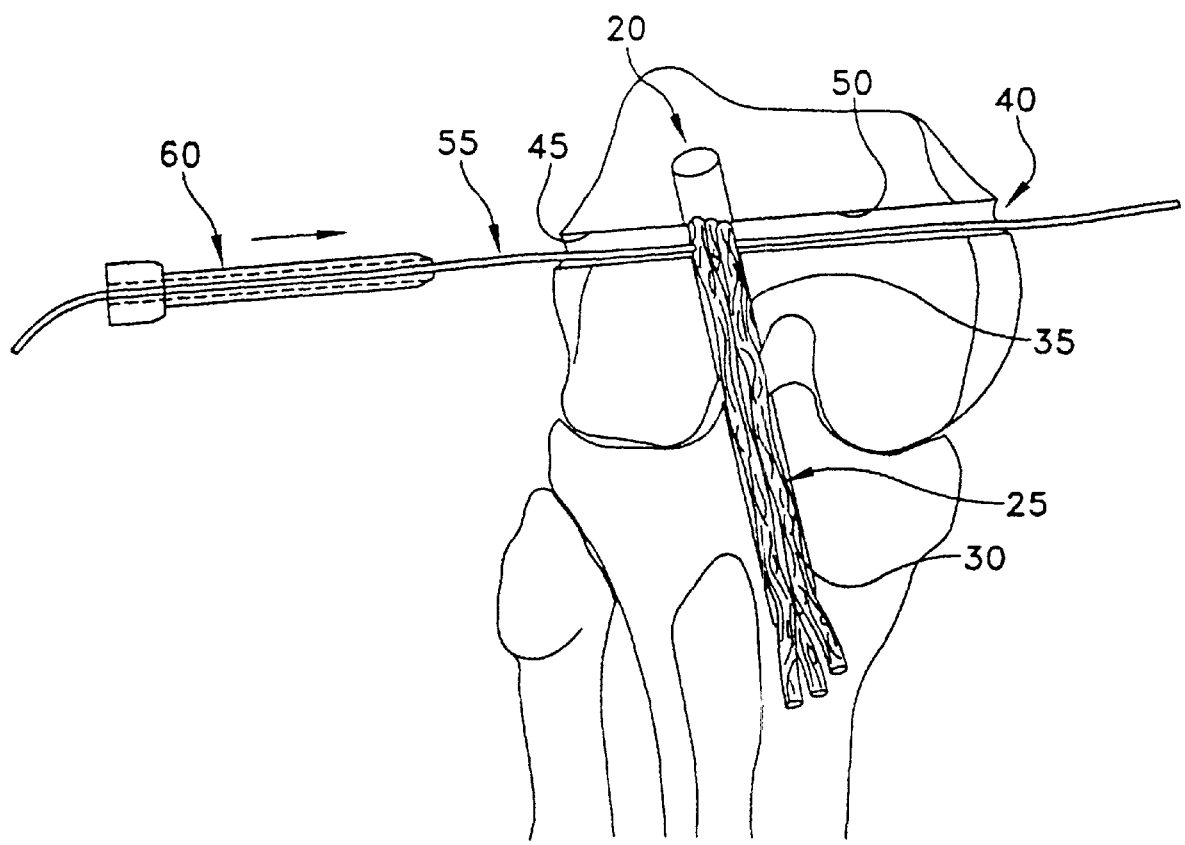
Figure 5:
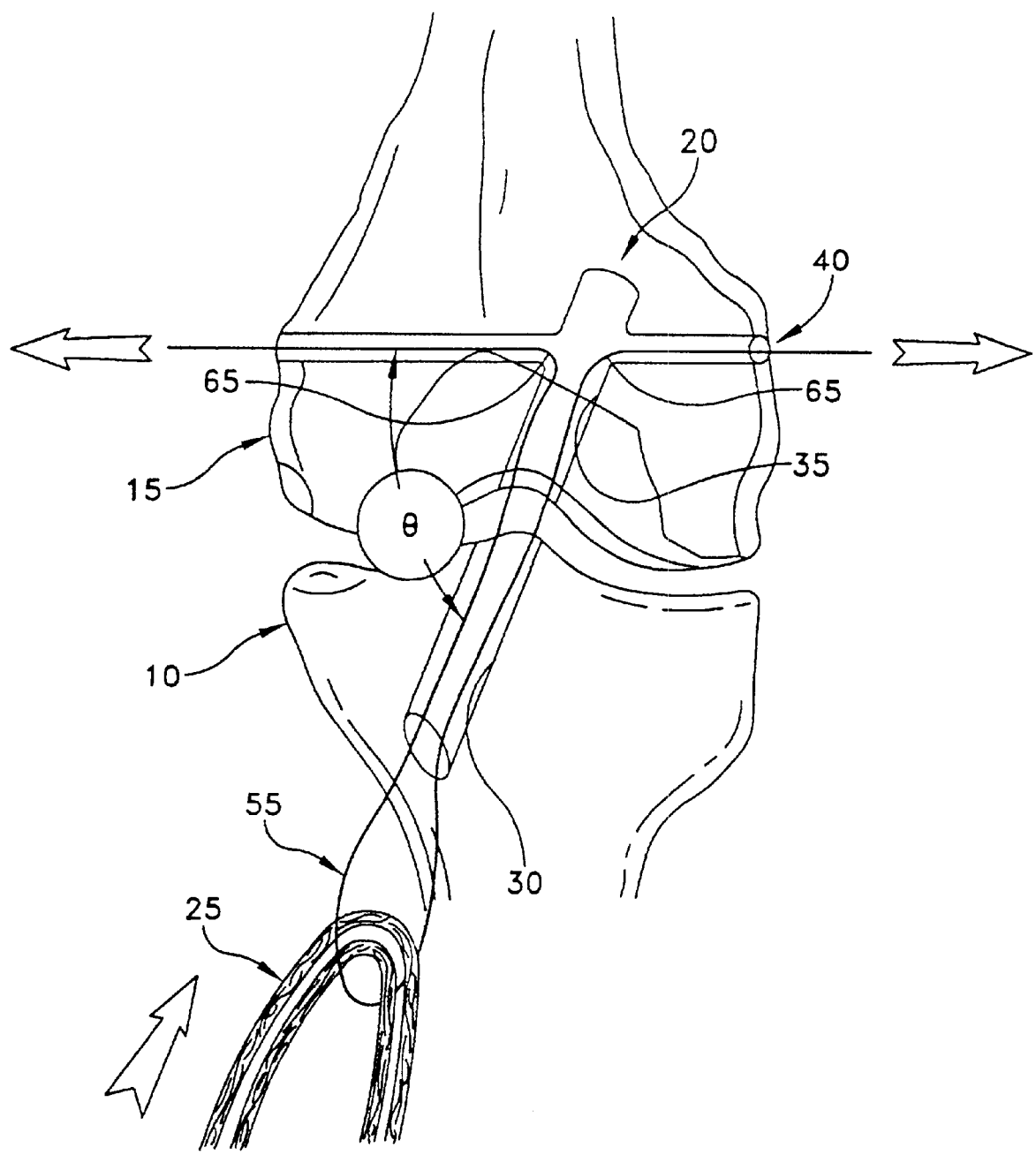
Figure 6:
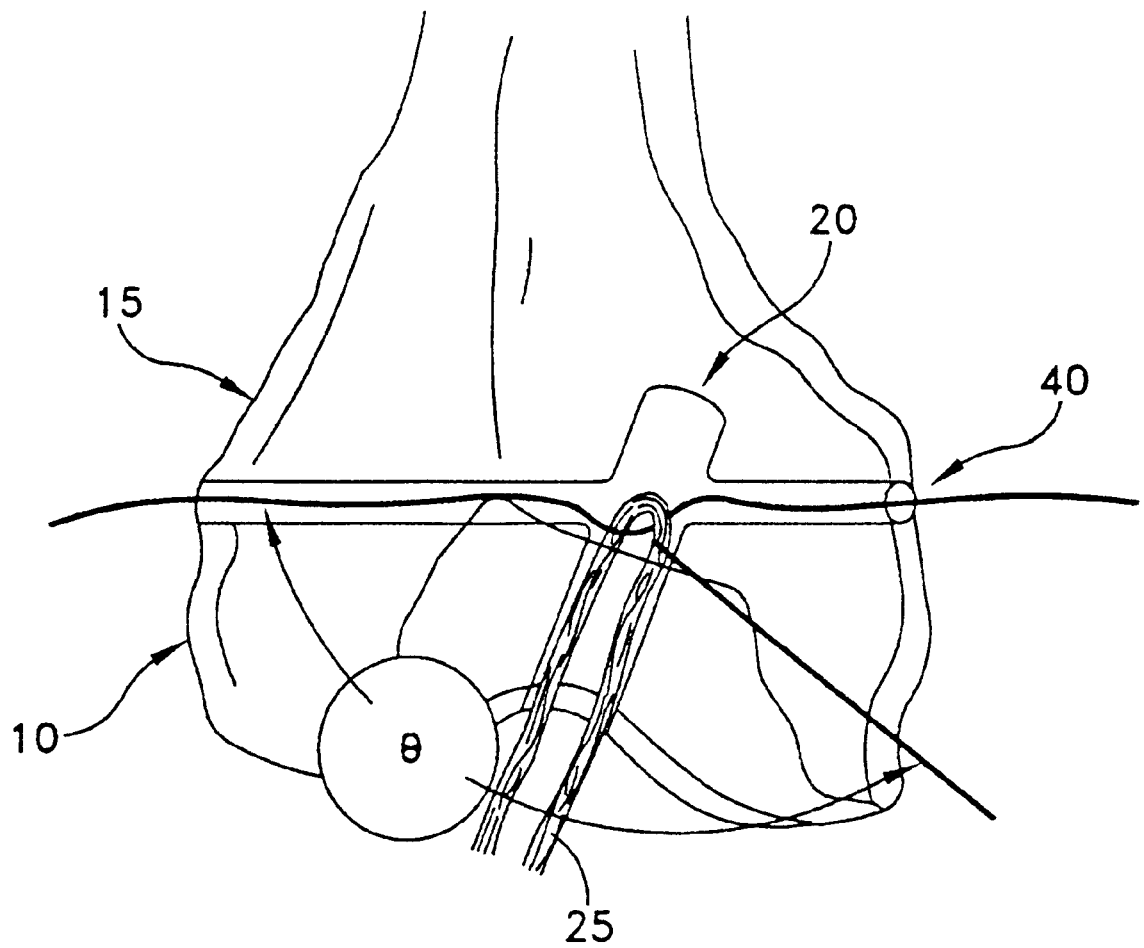
Figure 7:
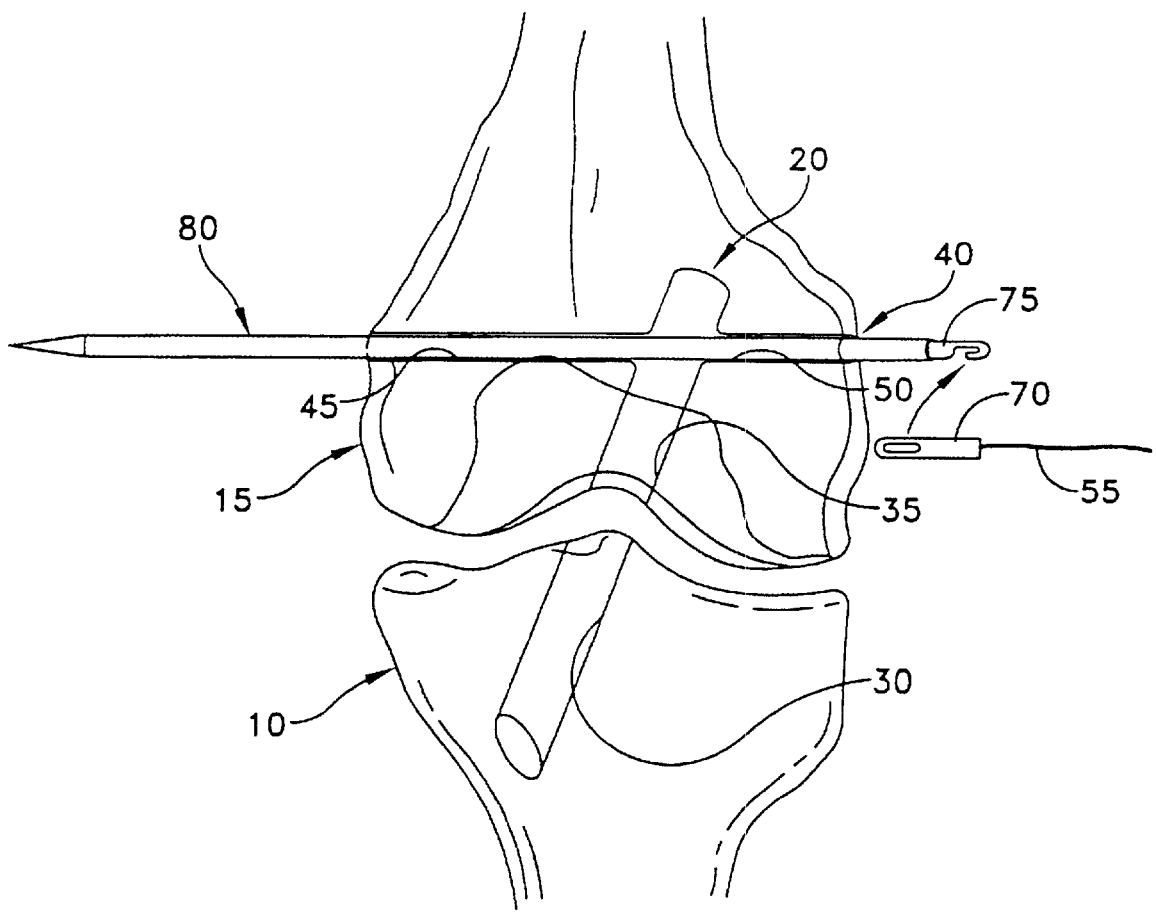
FIGS. 7–14 are schematic front views of a knee joint, illustrating a novel procedure for positioning a graft ligament in a bone tunnel and securing it in position.

More particularly, and looking now at FIG. 7, the bone tunnel 20 is formed by drilling through tibia 10 and up into femur 15, whereby to form tibial tunnel 30 and femoral tunnel 35. Then the transverse bone tunnel 40 is formed in femur 15 so that transverse bone tunnel 40 intersects femoral tunnel 35. Bone tunnel 20 bifurcates transverse bone tunnel 40 into two tunnel portions, a first transverse bone tunnel portion 45 and a second transverse bone tunnel portion 50.

Figure 8:
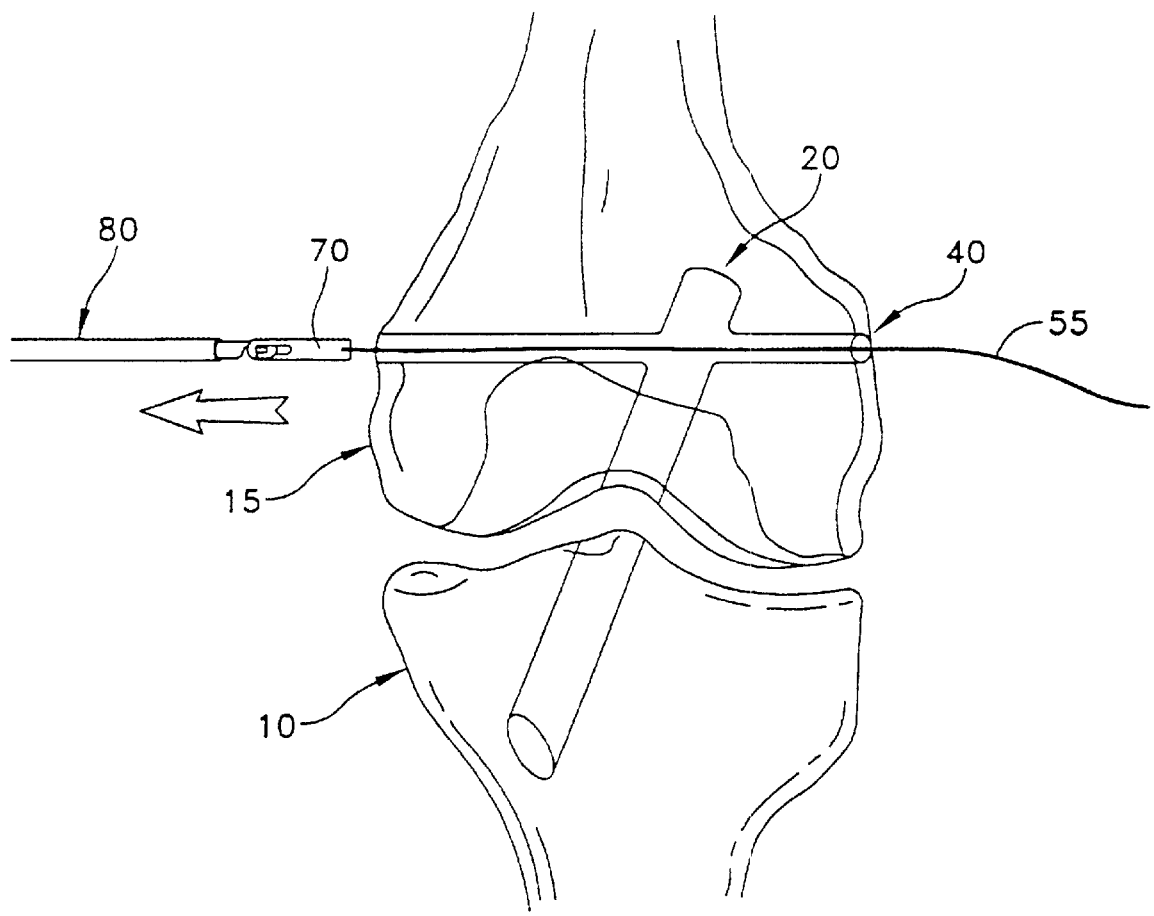

After transverse bone tunnel 40 has been formed, a flexible member 55 is passed across transverse bone tunnel 40. This may be done by attaching a distal end 70 of flexible member 55 to the proximal end 75 of a transverse drill pin 80, and then drawing flexible member 55 through transverse bone tunnel 40 in the manner shown in FIGS. 7 and 8.

Figure 9:
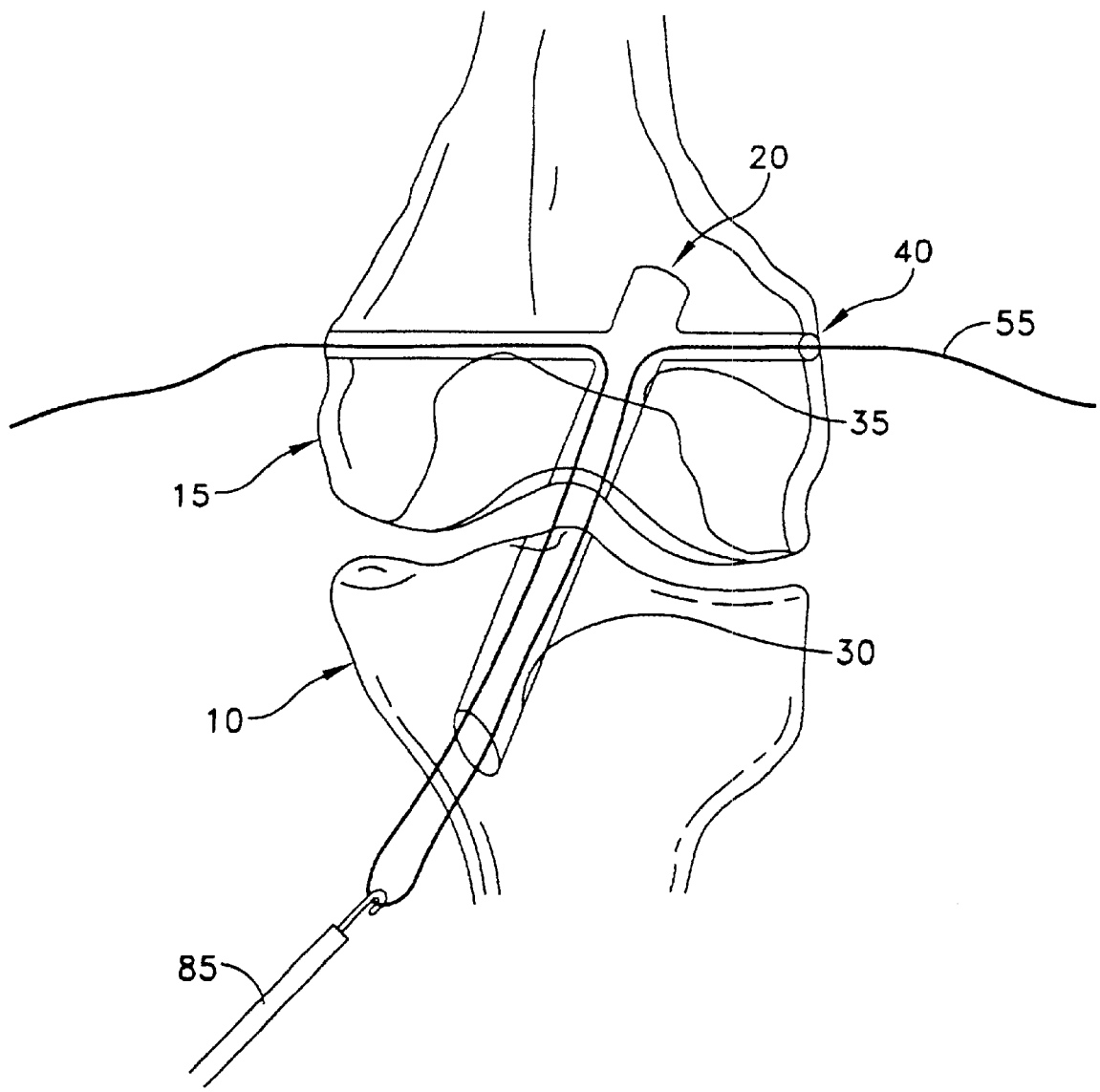

Next, a crochet-hook member 85 (FIG. 9) is passed up tibial tunnel 30, across the interior of the knee joint, and then up femoral tunnel 35 so as to hook flexible member 55 and draw it down femoral tunnel 35, across the interior of the knee joint, down tibial tunnel 30 and then out the bottom of tibial tunnel 30. See FIG. 9.

The end of flexible member 55 extending out of tibial tunnel 30, shown generally at 90, is set aside for future use. See FIG. 10.

Figure 10:
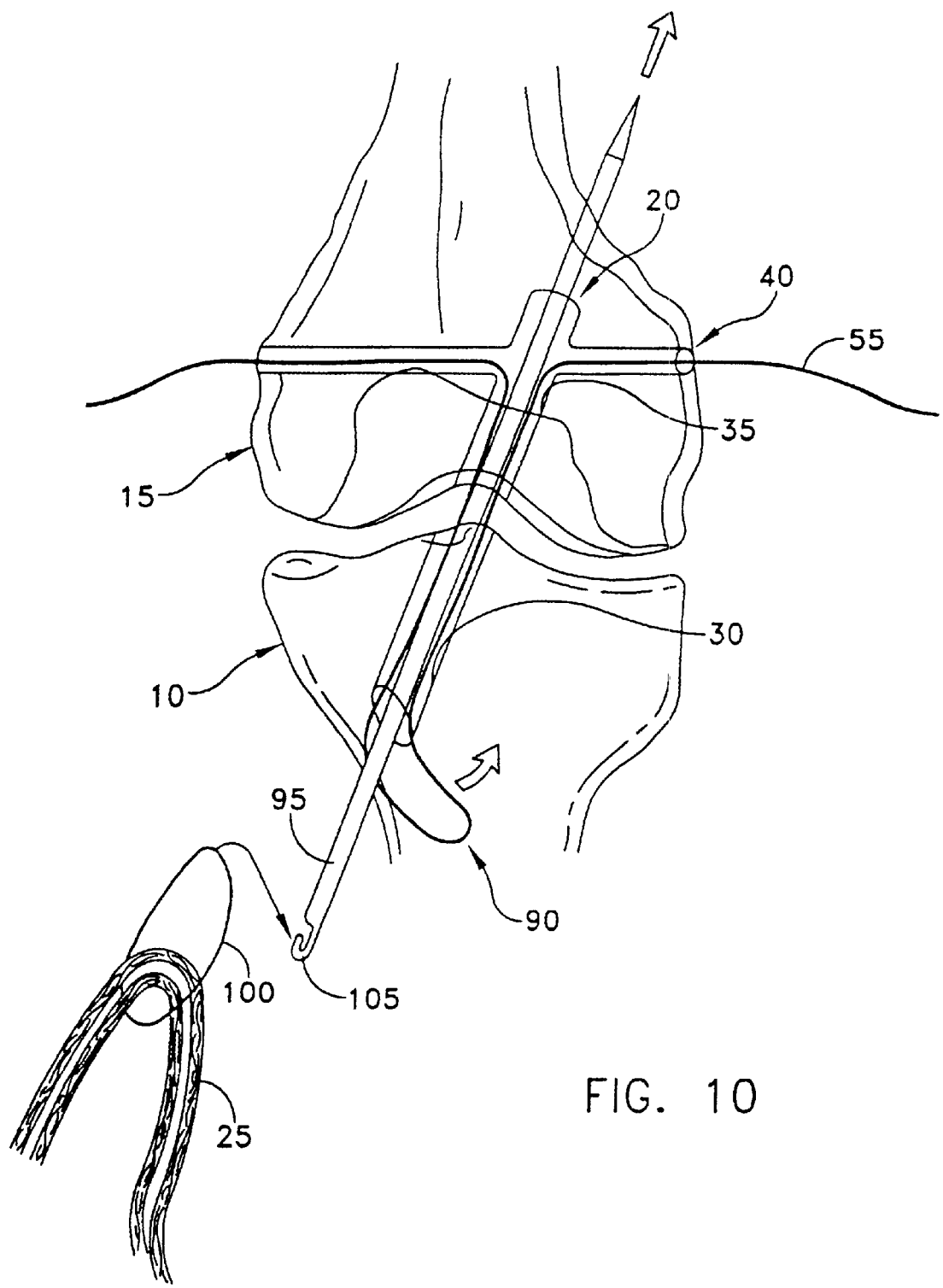

Next, and still looking now at FIG. 10, a second drill pin 95 is passed up tibial tunnel 30, across the interior of the knee joint, up femoral tunnel 35, and then drilled out the top of femur 15. Then graft ligament 25 is looped through a loop 100 of flexible material, and loop 100 is connected to the proximal end 105 of second drill pin 95. Then drill pin 95 is passed through the top of femur 15 so as to draw graft ligament 25 up tibial tunnel 30, across the interior of the knee joint, and up femoral tunnel 35. Second drill pin 95 may then be removed, with loop 100 holding graft ligament 25 in position within femoral tunnel 35 and tibial tunnel 30. See FIG. 11.

Figure 11:
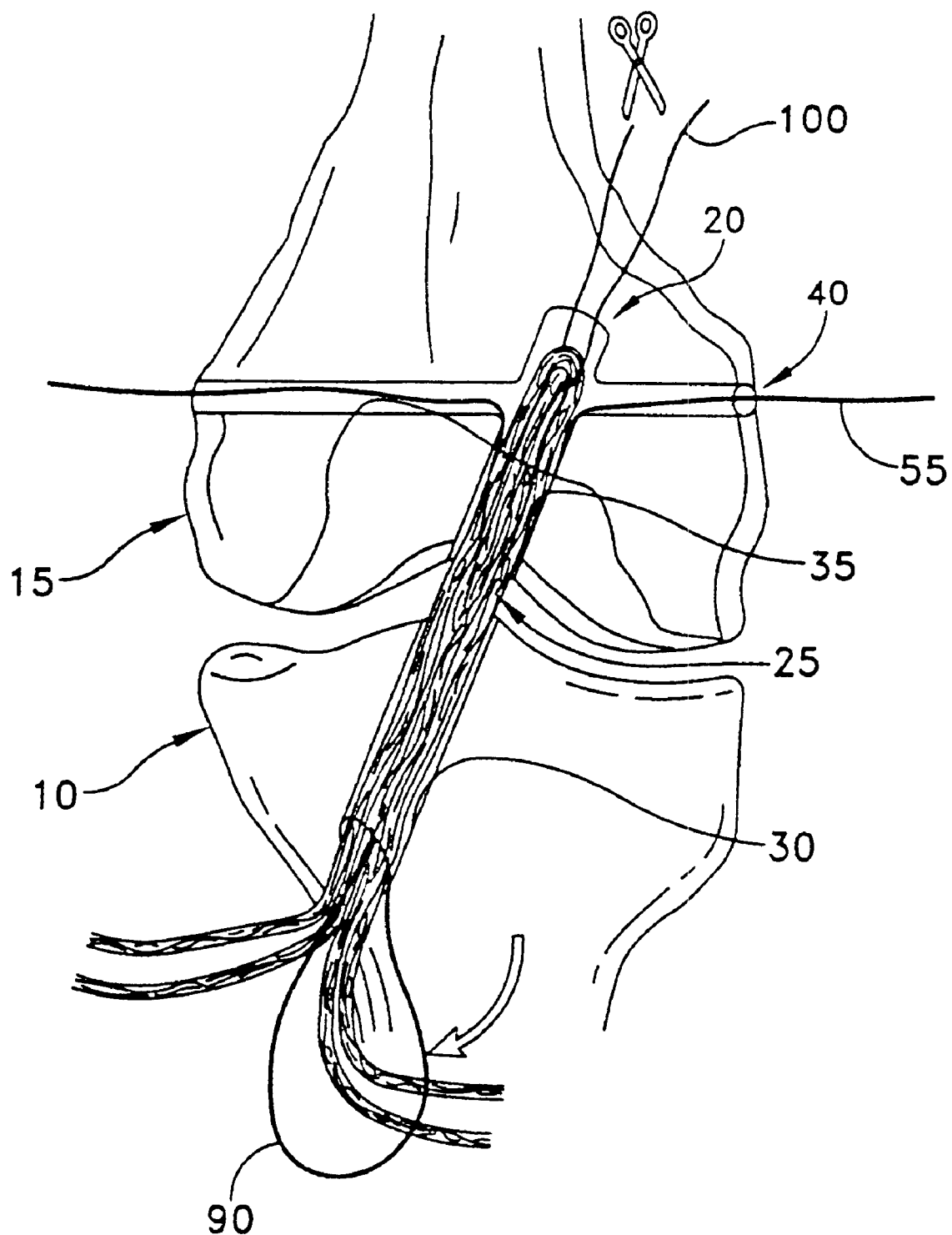
Figure 12:
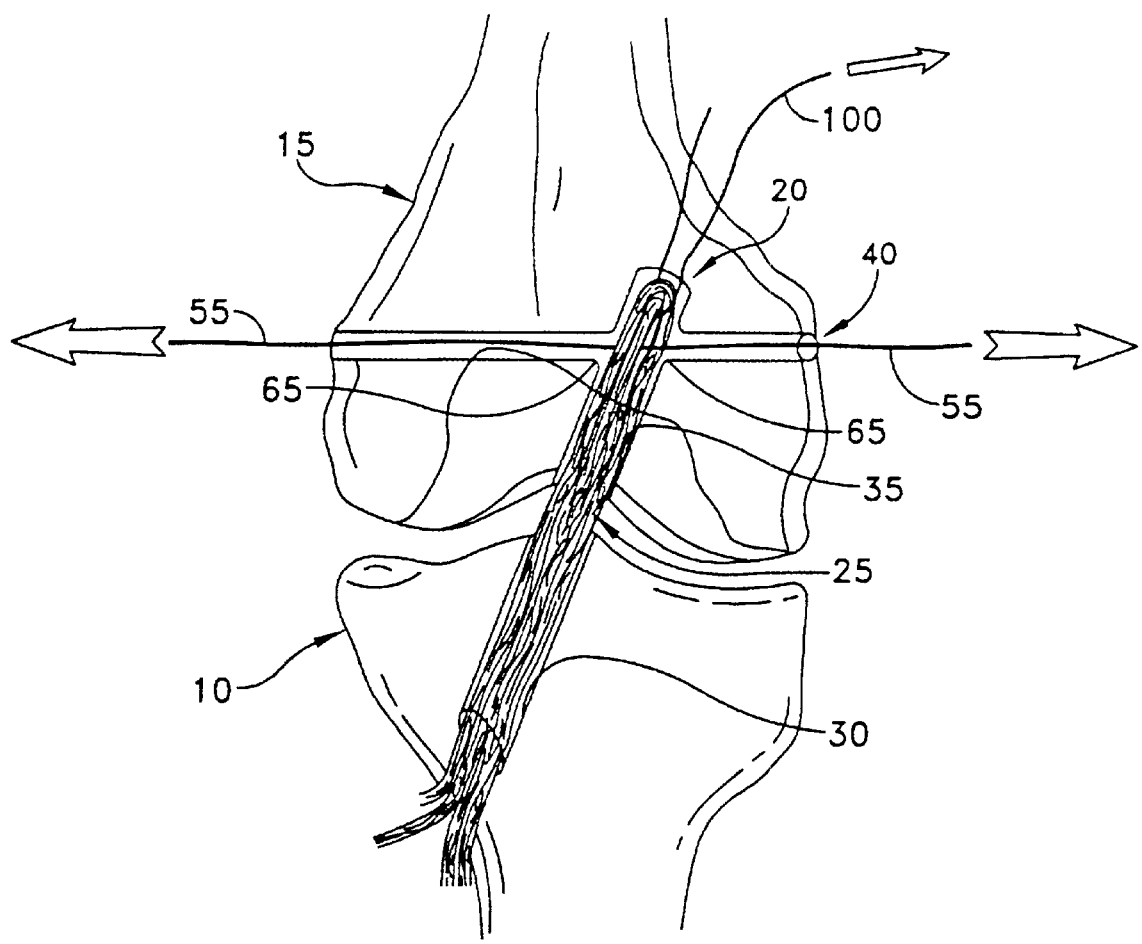
Figure 13:
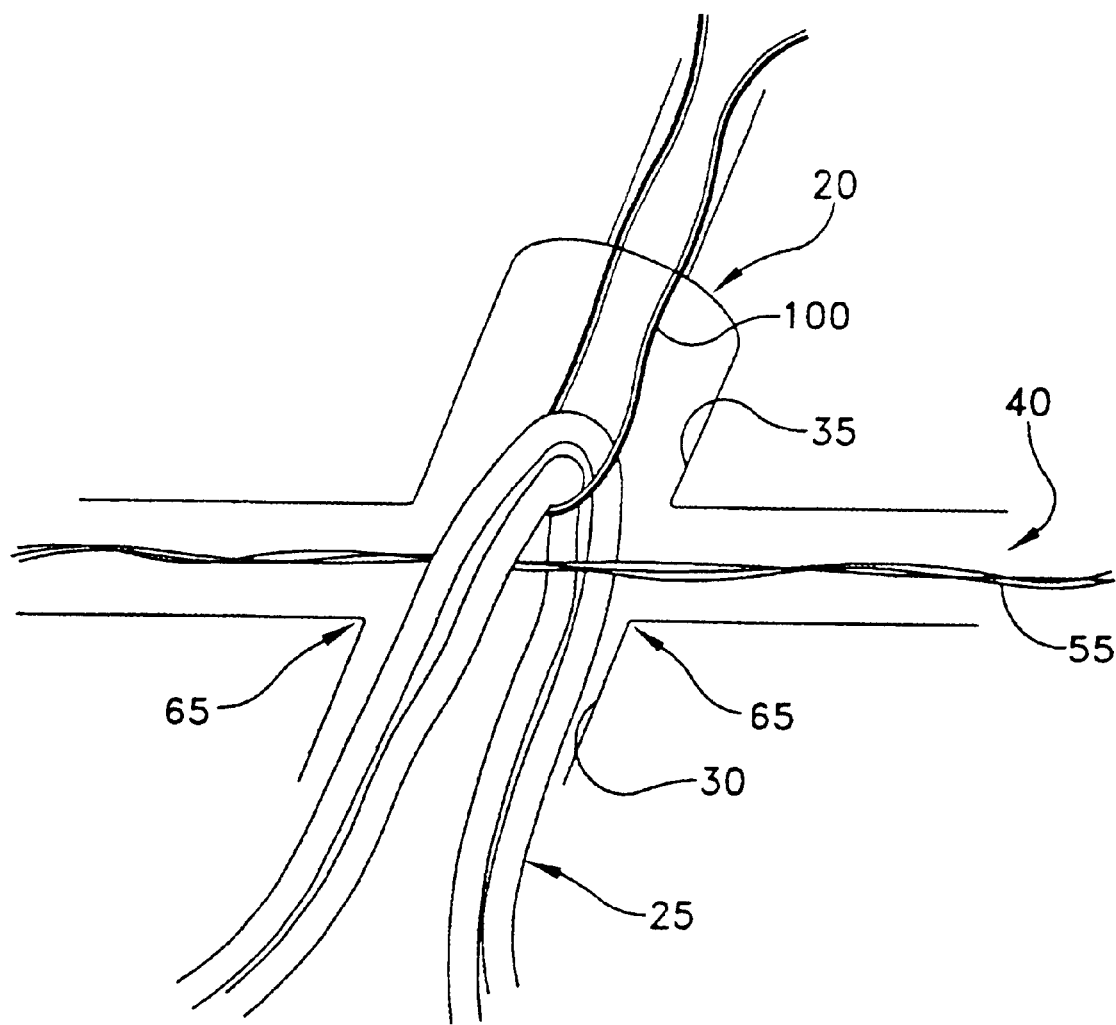

After graft ligament 25 has been positioned in the manner shown in FIG. 11, the end of flexible member 55 that extends out of tibial tunnel 30, shown generally at 90, is placed between the graft ligament strands. See FIG. 11. Then one or both of the free ends of flexible member 55 is/are pulled away from femur 15, in the manner shown in FIG. 12, whereby to pull flexible member 55 up tibial tunnel 30, across the interior of the knee joint, and up femoral tunnel 35 so as to achieve the position shown in FIGS. 12 and 13. In this respect it should be appreciated that while flexible member 55 is being drawn up tibial tunnel 30, across the interior of the knee joint, and up femoral tunnel 35, graft ligament 25 is being supported within bone tunnel 20 by loop 100. As a result, flexible member 55 may be drawn readily upward, with minimal erosion of bone edges 65 (FIGS. 12 and 13).

Figure 14:
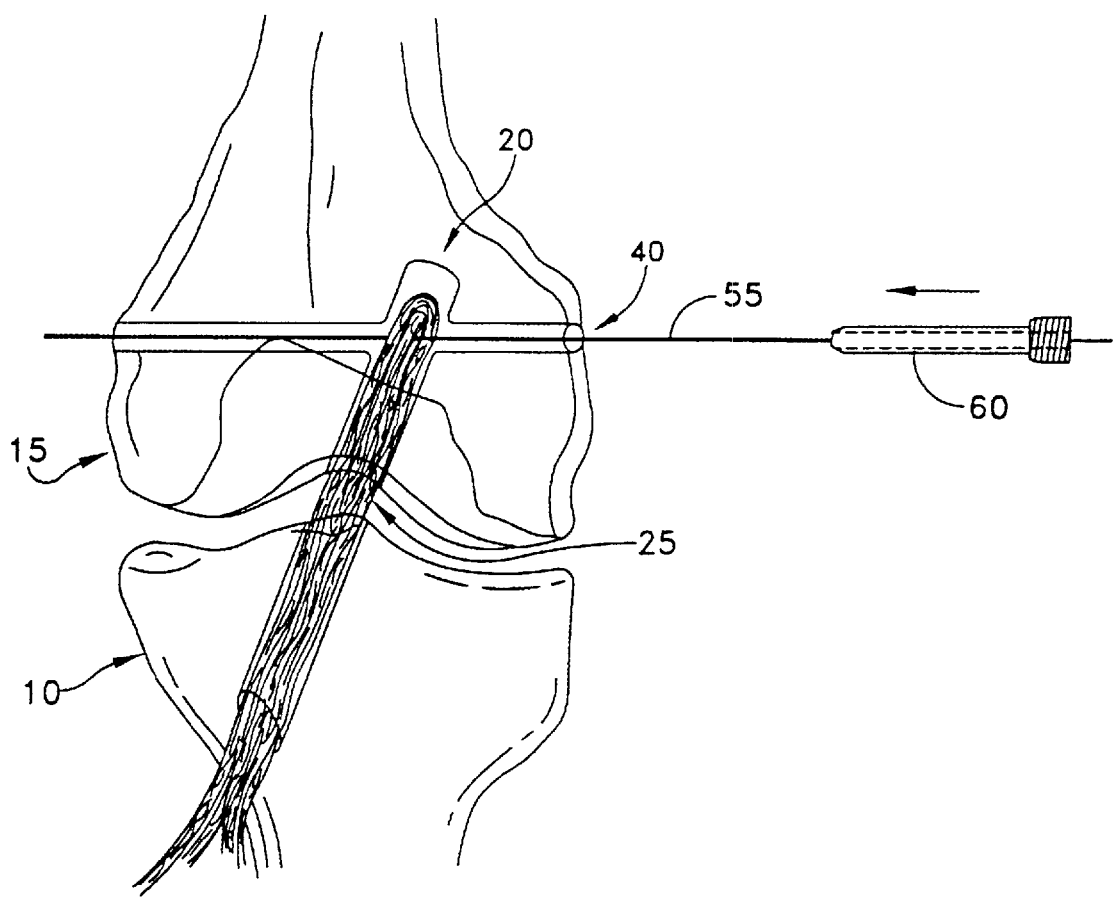

Looking next at FIG. 14, flexible member 55 is then used as a guide to pass a crosspin 60 through transverse bone tunnel 40 and, in the process, beneath looped graft ligament 25, whereby to support graft ligament 25 within bone tunnel 20. Loop 100 may thereafter be removed from graft ligament 25, and flexible member 55 removed from transverse bone tunnel 40. The proximal end of the graft ligament may thereafter be secured to tibia 10 in ways well known in the art so as to complete the ligament repair procedure.

ADVANTAGES OF THE INVENTION

Numerous advantages are achieved by using the present invention.

For one thing, since graft ligament 25 is pulled into bone tunnel 20 by the loop 100 moving along the line of bone tunnel 20, optimal force can be applied to lifting the graft ligament into position without damaging tunnel edges 65.

In addition, since flexible member 55 is used solely as a guide for crosspin 60, and is not used to lift graft ligament 25 within bone tunnel 20, flexible member 55 does not need to be strong enough to lift the graft ligament up the bone tunnel. As a result, flexible member 55 can be formed out of a wider range of materials and can have a smaller diameter, which in turn permits the cannulation in crosspin 60 to be smaller, which in turn permits the construction of a stronger crosspin.

Still other advantages of the present invention will be apparent to those skilled in the art.

MODIFICATION

It is to be understood that the present invention is by no means limited to the particular constructions and method steps disclosed above and/or shown in the drawings, but also comprises any modifications or equivalents within the scope of the claims.

What is claimed is:

1. A method for securing a graft ligament in a bone tunnel, said method comprising the steps of:
    (1) forming a first bone tunnel in a bone, and forming a second bone tunnel in the same bone, said second bone tunnel being transverse to, and intersecting, said first bone tunnel;

(2) positioning a flexible member in said second transverse bone tunnel so that said flexible member extends across said first bone tunnel, and positioning said graft ligament in said first bone tunnel, without removing said flexible member from said second transverse bone tunnel and independently of said flexible member, so that said graft ligament is looped over said flexible member; and (3) positioning a crosspin over said flexible member and in said second transverse bone tunnel so that said graft ligament is looped over, and may be supported by, said crosspin.

2. A method according to claim 1 wherein said step of positioning said graft ligament in said first bone tunnel, independently of said flexible member, comprises the sub-steps of:

(i) pulling a loop of said flexible member out of said first bone tunnel;

(b) pulling a loop of said graft ligament into said first bone tunnel so that said loop of graft ligament extends past the intersection of said second transverse bone tunnel with said first bone tunnel;

(c) positioning said loop of said flexible member within said loop of graft ligament; and (d) pulling said flexible member straight so as to eliminate said loop of said flexible member.

3. A method according to claim 2 wherein said sub-step of pulling said loop of said graft ligament into said first bone tunnel comprises the sub-sub-steps of:

(i) attaching said loop of said graft ligament to a pulling member; and (ii) passing said pulling member out the far said of said first bone tunnel.

4. A method for securing a graft ligament in a bone tunnel, said method comprising the steps of:

(1) forming a first bone tunnel in a bone, and forming a second bone tunnel in the same bone, said second bone tunnel being transverse to, and intersecting, said first bone tunnel;

(2) positioning a flexible member in said second transverse bone tunnel so that said flexible member extends across said first bone tunnel;

(3) pulling a loop of said flexible member out of said first bone tunnel;

(4) pulling a loop of said graft ligament into said first bone tunnel so that said loop of graft ligament extends past the intersection of said second transverse bone tunnel with said first bone tunnel;

(5) positioning said loop of said flexible member within said loop of graft ligament;

(6) pulling said flexible member straight so as to eliminate said loop of said flexible member; and (7) positioning a crosspin over said flexible member and in said second transverse bone tunnel so that said graft ligament is looped over, and may be supported by, said crosspin.

5. A method for securing a graft ligament in a bone tunnel, said method comprising the steps of:

(1) forming a first bone tunnel in a bone, and forming a second bone tunnel in the same bone, said second bone tunnel being transverse to, and intersecting, said first bone tunnel;

(2) positioning a flexible member in said second transverse bone tunnel so that said flexible member extends across said first bone tunnel, and positioning said graft ligament in said first bone tunnel, independently of said flexible member, so that said graft ligament is looped over said flexible member, said step of positioning said graft ligament in said first bone tunnel comprising the sub-steps of:

(a) pulling a loop of said flexible member out of said first bone tunnel;

(b) pulling a loop of said graft ligament into said first bone tunnel so that said loop of graft ligament extends past the intersection of said second transverse bone tunnel with said first bone tunnel;

(c) positioning said loop of said flexible member within said loop of graft ligament; and (d) pulling said flexible member straight so as to eliminate said loop of said flexible member; and (3) positioning a crosspin over said flexible member and in said second transverse bone tunnel so that said graft ligament is looped over, and may be supported by, said crosspin.

6. A method for securing a graft ligament in a bone tunnel, said method comprising the steps of:

(1) forming a first bone tunnel in a bone, and forming a second bone tunnel in the same bone, said second bone tunnel being transverse to, and intersecting, said first bone tunnel;

(2) positioning a flexible member in said second transverse bone tunnel so that said flexible member extends across said first bone tunnel, and positioning said graft ligament in said first bone tunnel, independently of said flexible member, so that said graft ligament is looped over said flexible member, said step of positioning said graft ligament in said first bone tunnel comprising the sub-steps of:

(a) pulling a loop of said flexible member out of said first bone tunnel;

(b) pulling a loop of said graft ligament into said first bone tunnel so that said loop of graft ligament extends past the intersection of said second transverse bone tunnel with said first bone tunnel, said sub-step of pulling said loop of graft ligament into said first bone tunnel comprising the sub-sub-steps of:

(i) attaching said loop of said graft ligament to a pulling member; and:

(ii) passing said pulling member out the far said of said first bone tunnel;

(c) positioning said loop of said flexible member within said loop of graft ligament; and (d) pulling said flexible member straight so as to eliminate said loop of said flexible member.

* * * * *